(12) United States Patent
France et al.

(10) Patent No.: US 10,232,087 B2
(45) Date of Patent: Mar. 19, 2019

(54) POROUS MATRIX

(75) Inventors: Richard Melville France, Nottingham (GB); Robin Andrew Quirk, Nottingham (GB)

(73) Assignee: LOCATE THERAPEUTICS LIMITED, Nottingham (GB)

( * ) Notice: Subject to any disclaimer, the term of this patent is extended or adjusted under 35 U.S.C. 154(b) by 1967 days.

(21) Appl. No.: 10/550,151

(22) PCT Filed: Mar. 29, 2004

(86) PCT No.: PCT/GB2004/001419
§ 371 (c)(1),
(2), (4) Date: Sep. 20, 2005

(87) PCT Pub. No.: WO2004/084968
PCT Pub. Date: Oct. 7, 2004

(65) Prior Publication Data
US 2006/0263335 A1 Nov. 23, 2006

(30) Foreign Application Priority Data
Mar. 27, 2003 (GB) .................................. 0307011.7

(51) Int. Cl.
| A61K 31/17 | (2006.01) |
| A61K 31/282 | (2006.01) |
| A61K 31/4164 | (2006.01) |
| A61K 31/7028 | (2006.01) |
| A61K 47/02 | (2006.01) |
| A61K 9/14 | (2006.01) |
| A61L 27/56 | (2006.01) |
| A61L 27/54 | (2006.01) |
| A61P 43/00 | (2006.01) |

(52) U.S. Cl.
CPC ............... *A61L 27/56* (2013.01); *A61L 27/54* (2013.01); *A61L 2300/254* (2013.01); *A61L 2300/406* (2013.01); *A61L 2300/414* (2013.01); *A61L 2300/43* (2013.01)

(58) Field of Classification Search
None
See application file for complete search history.

(56) References Cited

U.S. PATENT DOCUMENTS

| 4,938,763 A | 7/1990 | Dunn et al. |
| 4,997,443 A | 3/1991 | Walthall et al. |
| 5,077,049 A | 12/1991 | Dunn et al. |
| 5,278,201 A | 1/1994 | Dunn et al. |
| 5,278,202 A | 1/1994 | Dunn et al. |
| 5,286,495 A * | 2/1994 | Batich .................. A61K 9/1652 424/488 |
| 5,324,519 A | 6/1994 | Dunn et al. |
| 5,340,849 A | 8/1994 | Dunn et al. |
| 5,344,701 A * | 9/1994 | Gagnon et al. ............ 428/304.4 |
| 5,368,859 A | 11/1994 | Dunn et al. |
| 5,487,897 A | 1/1996 | Polson et al. |
| 5,502,092 A | 3/1996 | Susko et al. |
| 5,599,552 A | 2/1997 | Dunn et al. |
| 5,632,727 A | 5/1997 | Tipton et al. |
| 5,650,176 A | 7/1997 | Lee et al. |
| 5,660,849 A | 8/1997 | Polson et al. |
| 5,667,778 A | 9/1997 | Atala |
| 5,676,976 A | 10/1997 | Lee et al. |
| 5,677,284 A | 10/1997 | Li |
| 5,683,461 A | 11/1997 | Lee et al. |
| 5,702,716 A | 12/1997 | Tipton et al. |
| 5,709,854 A | 1/1998 | Griffith-Cima et al. |
| 5,725,491 A | 3/1998 | Tipton et al. |
| 5,733,950 A | 3/1998 | Tipton et al. |
| 5,739,176 A | 4/1998 | Dunn et al. |
| 5,976,526 A | 11/1999 | Atala |
| 6,027,742 A | 2/2000 | Lee et al. |
| 6,060,053 A | 5/2000 | Atala |
| 6,071,530 A | 6/2000 | Polson et al. |
| 6,117,456 A | 9/2000 | Lee et al. |
| 6,129,761 A * | 10/2000 | Hubbell ..................... 623/23.72 |
| 6,132,463 A | 10/2000 | Lee et al. |
| 6,139,578 A | 10/2000 | Lee et al. |
| 6,143,293 A | 11/2000 | Weiss et al. |
| 6,214,368 B1 | 4/2001 | Lee et al. |

(Continued)

FOREIGN PATENT DOCUMENTS

| CN | 1339289 | 3/2002 |
| DE | 69626979T T2 | 5/1996 |

(Continued)

OTHER PUBLICATIONS

Jacobs et al. 1993. Polymer Delivery Systems Concepts. Date: Mar. 5, 1993 | doi: 10.1021/bk-1993-0520.ch001 in Polymeric Delivery Systems; El-Nokaly, M., et al.; ACS Symposium Series; American Chemical Society: Washington, DC, 1993.*
Hutmacher. 2000. Scaffolds in tissue engineering bone and cartilage. Biomaterials, vol. 21, pp. 2529-2543.*
Yang et all. 2001.The Design of Scaffolds for Use in Tissue Engineering. Part I. Traditional Factors. Tissue Engineering, vol. 7, No. 6 pp. 679-689.*
Australian Patent Application No. 2004224547, applicant's response to Examiner's report dated Apr. 3, 2009, as filed Nov. 2, 2009.
Australian Patent Application No. 2004224547, Examiner's first report dated Apr. 3, 2009.

*Primary Examiner* — Robert J Yamasaki
(74) *Attorney, Agent, or Firm* — Procopio, Cory, Hargreaves & Savitch LLP

(57) ABSTRACT

A porous matrix suitable for use as a tissue scaffold is described. The matrix may be shaped before insertion into or at the target tissue site, or injected via a minimally invasive method. The matrix may be pre-seeded with cells of the target tissue or may be used to support growth of the local endogenous tissue. The matrix may contain growth factors or other pharmacologically acceptable moieties such as antibiotics.

11 Claims, 3 Drawing Sheets

(56) References Cited

U.S. PATENT DOCUMENTS

| | | |
|---|---|---|
| 6,224,893 B1 | 5/2001 | Langer et al. |
| 6,277,151 B1 | 8/2001 | Lee et al. |
| 6,287,341 B1 | 9/2001 | Lee et al. |
| 6,290,729 B1 * | 9/2001 | Slepian et al. ............ 623/23.72 |
| 6,306,169 B1 * | 10/2001 | Lee et al. .................. 623/11.11 |
| 6,331,312 B1 | 12/2001 | Lee et al. |
| 6,376,742 B1 | 4/2002 | Zdrahala et al. |
| 6,395,293 B2 | 5/2002 | Polson et al. |
| 6,471,993 B1 * | 10/2002 | Shastri ................ A61K 38/465 424/422 |
| 6,534,084 B1 * | 3/2003 | Vyakarnam et al. ......... 424/443 |
| 6,541,037 B1 | 4/2003 | Lee et al. |
| 6,544,290 B1 | 4/2003 | Lee et al. |
| 6,638,312 B2 | 10/2003 | Plouhar et al. |
| 6,703,038 B1 | 3/2004 | Schaefer et al. |
| 6,730,298 B2 | 5/2004 | Griffith-Cima et al. |
| 6,818,018 B1 * | 11/2004 | Sawhney ................ 623/11.11 |
| 6,841,617 B2 * | 1/2005 | Jeong et al. ................ 524/845 |
| 6,903,146 B2 | 6/2005 | Matsushima et al. |
| 6,953,594 B2 | 10/2005 | Lee et al. |
| 6,972,130 B1 | 12/2005 | Lee et al. |
| 9,486,558 B2 * | 11/2016 | France .................... A61L 27/54 |
| 2001/0016772 A1 | 8/2001 | Lee et al. |
| 2001/0055588 A1 | 12/2001 | Griffith-Cima et al. |
| 2002/0001608 A1 | 1/2002 | Polson et al. |
| 2002/0004573 A1 | 1/2002 | Domschke et al. |
| 2002/0076443 A1 | 1/2002 | Stein et al. |
| 2002/0055143 A1 | 5/2002 | Bell et al. |
| 2002/0136696 A1 | 9/2002 | Lee et al. |
| 2002/0155137 A1 | 10/2002 | Lee et al. |
| 2002/0155167 A1 | 10/2002 | Lee et al. |
| 2002/0164374 A1 | 11/2002 | Jackson et al. |
| 2002/0183858 A1 * | 12/2002 | Contiliano et al. ........ 623/23.76 |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0044444 A1 | 3/2003 | Malaviya et al. |
| 2003/0049299 A1 | 3/2003 | Malaviya et al. |
| 2003/0078617 A1 | 4/2003 | Schwartz et al. |
| 2003/0082232 A1 | 5/2003 | Lee et al. |
| 2003/0104031 A1 | 6/2003 | Dumont et al. |
| 2003/0215946 A1 | 11/2003 | Nair et al. |
| 2004/0059431 A1 | 3/2004 | Plouhar et al. |
| 2004/0101960 A1 | 5/2004 | Schaefer et al. |
| 2004/0143344 A1 | 7/2004 | Malaviya et al. |
| 2004/0166169 A1 | 8/2004 | Malaviya et al. |
| 2004/0170612 A1 | 9/2004 | Griffith et al. |
| 2004/0220574 A1 | 11/2004 | Pelo et al. |
| 2004/0234571 A1 | 11/2004 | Jang |
| 2004/0258729 A1 | 12/2004 | Czernuszka et al. |
| 2005/0027307 A1 | 2/2005 | Schwartz et al. |
| 2005/0038492 A1 | 2/2005 | Mason et al. |
| 2005/0042293 A1 | 2/2005 | Jackson et al. |
| 2005/0238683 A1 | 10/2005 | Adhikari et al. |
| 2006/0067969 A1 | 3/2006 | Lu et al. |
| 2006/0136071 A1 | 6/2006 | Maspero et al. |

FOREIGN PATENT DOCUMENTS

| | | |
|---|---|---|
| DE | 19956503 A1 | 11/1999 |
| DE | 69626979 | 2/2004 |
| DE | 69433843 T2 | 6/2005 |
| DE | 69729647 | 7/2005 |
| DE | 69533404 | 9/2005 |
| DE | 60108818 | 2/2006 |
| EP | 0484387 B1 | 5/1992 |
| EP | 0539751 B1 | 10/1992 |
| EP | 0649662 B1 | 8/1994 |
| EP | 0784490 B1 | 7/1997 |
| EP | 0831867 B1 | 1/1998 |
| EP | 0936929 B1 | 8/1999 |
| EP | 1231947 B1 | 5/2001 |
| EP | 1147781 B1 | 10/2001 |
| EP | 1177800 B1 | 6/2002 |
| EP | 1554989 A1 | 12/2004 |
| GB | 0215832 | 2/1923 |
| GB | 2370777 B | 10/2002 |
| WO | WO9101126 A1 | 2/1991 |
| WO | WO9425080 A1 | 11/1994 |
| WO | WO9610374 A1 | 4/1996 |
| WO | WO9610428 A1 | 4/1996 |
| WO | WO9636562 A1 | 11/1996 |
| WO | WO9639159 A1 | 12/1996 |
| WO | WO9640304 A1 | 12/1996 |
| WO | WO9816209 A3 | 4/1998 |
| WO | WO9816268 A3 | 4/1998 |
| WO | WO9840111 A1 | 9/1998 |
| WO | WO9852543 A1 | 11/1998 |
| WO | WO9909149 A9 | 2/1999 |
| WO | WO9911196 A1 | 3/1999 |
| WO | WO9921908 A1 | 5/1999 |
| WO | WO9925391 | 5/1999 |
| WO | WO9948541 A1 | 9/1999 |
| WO | WO0007639 A1 | 2/2000 |
| WO | WO0015194 A1 | 3/2000 |
| WO | WO0034454 A3 | 6/2000 |
| WO | WO0064977 | 11/2000 |
| WO | WO0137889 A3 | 5/2001 |
| WO | WO0138428 A1 | 5/2001 |
| WO | WO0197865 A3 | 12/2001 |
| WO | WO0200275 A1 | 1/2002 |
| WO | 2002/20645 A2 | 3/2002 |
| WO | WO02058754 A1 | 8/2002 |
| WO | WO03007784 A3 | 1/2003 |
| WO | WO03007786 A2 | 1/2003 |
| WO | WO03007787 A3 | 1/2003 |
| WO | WO03007788 A3 | 1/2003 |
| WO | WO03007789 A3 | 1/2003 |
| WO | WO03007790 A3 | 1/2003 |
| WO | WO03007806 A3 | 1/2003 |
| WO | WO03007839 A3 | 1/2003 |
| WO | WO03007847 A1 | 1/2003 |
| WO | WO03007879 A3 | 1/2003 |
| WO | WO03022319 A1 | 3/2003 |
| WO | WO03024316 A2 | 3/2003 |
| WO | WO03045351 A1 | 6/2003 |
| WO | WO03047647 A1 | 6/2003 |
| WO | WO03053216 A3 | 7/2003 |
| WO | WO04005355 A1 | 1/2004 |
| WO | WO04009227 A3 | 1/2004 |
| WO | WO05086706 A3 | 9/2005 |
| WO | WO06082442 A1 | 8/2006 |

* cited by examiner

POROUS MATRIX

CROSS-REFERENCE TO RELATED APPLICATIONS

This application claims priority to International Patent Application No. PCT/GB2004/001419 filed on Mar. 29, 2004. that claims the benefit of Great Britain Patent Application No. GB 0307011.7 filed Mar. 27, 2003, each of which are incorporated herein by reference in their entirety.

BACKGROUND OF THE INVENTION

Field of the Invention

This invention relates to a porous matrix. More particularly, the present invention relates to porous matrices which are intended to be used in the animal body and which are formed in situ at a target tissue site.

Description of the Related Art

Many patent applications describe the use of gels or sols, especially hydrogels, for use as tissue scaffolds. For example, WO 00/23054 describes the use of polyvinyl alcohol microspheres in the occlusion of blood vessels or embolizations. WO 99/15211 and WO 00/64977 describe the use of hydrogels as a tissue scaffold. The hydrogels are implanted into a patient in order to support tissue growth and or repair.

The use of hydrogels as tissue scaffolding is problematical in that although the gels themselves may adequately fill the cavity into which they are inserted, they have poor diffusion properties and as such drugs, nutrients or other factors to be supplied to the tissue do not adequately diffuse through the gel. This problem is exacerbated where the gel is seeded with living cells since the poor diffusion of nutrients can lead to premature cell death, possibly resulting in failure of the treatment. A further problem associated with gel scaffolds is that the cross-linking methods used to stabilise or solidify the gels, especially in situ, can damage the entrapped cells.

Scaffolds based on water-insoluble polymers are also known in the art, for example WO 99/25391 describes the use of poly (lactide-co-glycolide) (PLGA) as a polymer scaffold for the regeneration of tissue, especially bone tissue. The polymers are processed so as to form a porous structure. As with the hydrogels, the water-insoluble polymers are implanted into a patient in order to support tissue growth and or repair.

However, the disadvantage of such water-insoluble polymers is that they can only fill cavities with an open shape and methods of shaping the materials are yet to be perfected. Additionally, where the scaffold is to be seeded with cells, the seeding is inefficient (few pores are filled with cells) or the cells are damaged by the structure during the seeding process, and the surrounding tissue cells may also be damaged by the implantation procedures.

WO 99/11196 describes the use of a particulate matrix as tissue scaffold, the particles having internal cross-linking to stabilise the structure of the particle.

Similarly, PCT/GB02/02813 describes an open porous matrix of particulate material for in vivo use in or on a target tissue in medicine, the matrix comprising particles cross-linked with one another so as to define pores therebetween.

SUMMARY OF THE INVENTION

The present invention provides a process for the production of a porous matrix, the process comprising the steps of:

bringing a first phase into a fluid state,
introducing a second phase to the first phase,
mixing the first and second phases to ensure the required distribution of the second phase through the first phase is achieved, and
allowing the first phase to solidify or change state, with the second phase therein.

Advantageously, this process allows the matrix to be shaped or partially shaped before insertion into or onto the target tissue.

The term "fluid" as used herein is intended to define any substance which flows and therefore includes liquids, gases and solids (e.g. in powder or granule or grain form, or plastic solids) which are able to flow and to conform to the outline of their container.

The term "solidify" as used herein is intended to define that the phase becomes solid or semi-solid.

The first phase may be a carrier phase in that the phase carries or contains the material of the second phase, or it may be a coating phase which coats the material of the second phase. Preferably, the first phase is not in a liquid or wholly liquefied state but is, or is rendered, sufficiently fluid to mix with and to carry or coat the second phase. For example, the first phase may be fluid but tacky and coat the particulate material of the second phase. Alternatively, both the first and second phases may be in particulate or powder form and mixed together. In this case it is again desirable that the first phase is soft or tacky or otherwise able to coat any particulate material of the second phase.

Preferably, the first phase transforms from a fluid state to a solid or semi-solid state on the change of a single parameter, for example temperature, pH, introduction of a cross-linking, setting or gelling agent, presence/absence of light, ultra-violet curing or under anaerobic conditions. Most preferably, the first phase transforms due to a change in temperature or in pH, or the introduction of a cross-linking, setting or gelling agent. Where temperature is used it is preferred that the temperature is sufficient to render the phase workable but not to damage the surrounding tissues when used. A pre-use sintering step may be applied to either phase. The second phase is preferably a solid phase, but a liquid phase may be used, especially where the liquid is an emulsion or suspension of particulate material. Where the porous matrix is to be used as a tissue scaffolding matrix, the second phase optionally contains cells for the formation of new tissue.

However, the present inventors have found that the matrix may be used as a tissue scaffold without the need to introduce cells. When the tissue scaffold (without cells) is placed in or at a site where it is needed, local endogenous cells can be recruited or encouraged to grow on, in or about the scaffold causing new growth of the existing tissue. This effect is enhanced by the presence of appropriate growth factors being present in the scaffold. Such a situation is particularly useful since there is a much lower chance of rejection, or other immune reaction, of the new tissue than when introducing non-endogenous tissue. Hence, the need for treating a patient with immune suppressants can be reduced and the problems associated therewith can be reduced. Additionally, this technique is useful in patients who are already immune compromised such as cancer patients, the very young, the elderly, pregnant women or people suffering from AIDS or hepatitis B.

Accordingly, the present invention further provides a tissue scaffolding matrix, the matrix comprising a first phase and a second phase contained within the first phase. Preferably, the tissue scaffolding matrix is prepared according to the above described method.

The first and second phases used in the invention may be made from similar materials, with different solidifying or setting properties. For example, the first and second phases may be made from similar polymers with different gelling pHs or different melting temperatures or glass transition points.

Generally, one or both of the phases of the invention will comprise one or more polymers. Examples of synthetic polymers usable in the present invention include: poly($\alpha$-hydroxyacids) especially polylactic or polyglycolic acids, poly-lactide poly-glycolide copolymers, poly-lactide poly-ethylene glycol (PEG) copolymers; other polyesters including poly ($\epsilon$-caprolactone), poly (3-hydroxybutyrate), poly (s-caproic acid), poly (p-dioxanone) and poly (propylene fumarate); poly (ortho esters) including polyol/diketene acetals addition polymers (as described by Heller ACS Symposium Series 567, 292-305, 1994); polyanhydrides including poly (sebacic anhydride) (PSA), poly (carboxy-biscarboxyphenoxyphenoxyhexane) (PCPP), poly [bis (p-carboxyphenoxy) methane] (PCPM) and copolymers of SA, CPP and CPM (as described by Tamada and Langer in Journal of Biomaterials Science Polymer Edition, 3, 315-353, 1992 and by Domb in Chapter 8 of the Handbook of Biodegradable Polymers, ed. Domb A. J. and Wiseman R. M., Harwood Academic Publishers); poly (amino acids); poly (pseudo amino acids) (Including those described by James and Kohn at pages 389-403 of Controlled Drug Delivery Challenges and Strategies, American Chemical Society, Washington D.C.); polyphosphazenes including: derivatives of poly [(dichloro) phosphazene], poly [(organo) phosphazenes] polymers (described by Schacht in Biotechnology and Bioengineering, 52, 102-108, 1996); polyphosphates; polyethylene glycol polypropylene block co-polymers (for example that sold under the trade name Pluronics™).

Natural polymers may also be used, such as silk, elastin, chitin, chitosan, fibrin, fibrinogen, polysaccharides (including pectins), alginates, collagen, poly (amino acids), peptides, polypeptides or proteins.

Co-polymers prepared from the monomers of these polymers may also be used, as may random blends of these polymers or mixtures or combinations thereof.

The polymers may be crosslinked by a variety of methods including for example: UV crosslinking of acrylate polymers, Michael addition reaction of thiolate or acrylate polymers, thiolates polymers cross-linked via vinyl sulphones, cross-linking via succinimates or vinyl sulphones, crosslinking via hydrazines, thermally induced gelation, enzymatic crosslinking (for example the addition of thrombin to fibrinogen), cross-linking via the addition of salts or ions, (especially $Ca^{2+}$ ions), cross-linking via isocyanates, (for example hexamethylene diisocyanate).

In a preferred embodiment polyesters of poly (lactic-co-glycolic) acid (PLGA) are used. These polymers are approved for parenteral administration by the FDA. Because PLGA degrades via non-enzymatic hydrolysis in the initial stages, in vivo degradation rates can be predicted from in vitro data. PLGA degrades to lactic and glycolic acids, substances found naturally in the body.

However, polyesters may be the polymer system of choice for some embodiments. When the polyester material has broken down to molecular weights of about 5000 Daltons, the material may be taken up by cells, including macrophages, so some inflammation may be associated with the breakdown of these polymers.

Copolymers with amino acids may be synthesised, for example glycolic acid and glycine, or lactic acid and lysine (Barrera et al (1993) J Am Chem Soc 115, 11010-11011 and Cook et al (1997) J Biomed Mat Res 35, 513-523). These may be useful for immobilising other molecules, for example via the lysyl s-amino moieties. These polymers may be used to attach peptides to surfaces using covalent bonds. For example, peptides may be attached to poly (lactic acid-co-lysine) using 1,1'-carbonyl-diimidazole (CDI, Aldrich) as a linking agent as described in the above references.

By manipulating the molar ratio of lactic and glycolic acid and the molecular weight of the copolymers, different degradation patterns can be obtained. Poly-L-lactide has a degradation time in vitro of months to years. The long degradation time is due to its high crystallinity which protects the polymer from water penetration. Poly-glycolide has a degradation time of one to several months, whereas poly-D, L-lactide is amorphous and has a degradation time of one to a few months. D, L PLGA has a degradation time in vitro of weeks to months. As the glycolic acid ratio is increased, the rate of degradation increases. Homopolymers of s-caproic acid can remain intact for 2-3 year periods of implantation.

Preferably, at least one of the phases further comprises a plasticiser, examples of which include polyethylene glycol (PEG), polypropylene glycol, polycaprolactone low molecular weight oligomers of those polymers or conventional plasticisers such as those used extensively for commodity plastics materials which include but are not limited to adipates, phosphates, phthalates, sabacates, azelates and citrates. Plasticisers which are the same as the polymers used to form the first or second phases such as poly lactides, lactide-co-glycolide etc may also be used.

The second phase will generally comprise the tissue cells necessary to seed or form the tissue scaffold. The cells may be seeded into a particulate material comprising, entrained or carried within the second phase.

It is possible to use any animal cell in the tissue scaffold of the present invention. Examples of cells which may be used include but are not limited to bone, osteoprogenitor cells (for example from bone), cartilage, muscle, liver, kidney, skin, endothelial cells, gut or intestinal cells, or specialised cells such as cardiovascular cells, cardiomyocytes, pulmonary or other lung cells, placental, amnionic, chorionic or foetal cells, stem cells, chondrocytes, or reprogrammed cells from other parts of the body such as adipocytes reprogrammed to become cartilage cells.

Where stem cells are used, they are preferably non-embryonic stem cells such as those from adult bone marrow or the cornea or other endogenous stem cells, preferably taken from the patient to be treated.

The present inventors have noted in experiments that osteoprogenitor cells in an in vitro environment under certain conditions will produce cartilage in addition to bone which facilitates endochondral ossification which will allow the tissue engineering of a bone-cartilage interface.

Particles which may be used in the second phase to contain or introduce the cells may be of the type described in co-pending patent application PCT/GB02/02813.

Where particulate material is used in the second phase, it is preferred that the particles are porous. Preferably, the porosity of the particle is at least 10%, and more preferably is above 40%, and ideally may even be as high as 70 to 97%. A convenient working range may be of between 50 to 95%.

In any event it is preferred that the pore size of the particle is at least sufficient to receive the cells to be held therein. The cells may be added to the matrix at, or prior to, implantation of the matrix or afterwards in the case of recruitment from endogenous cells in situ.

Generally, the particles will be micro-particles; although where large cells are to be used the particles may be in the mm range.

The particles may be created using supercritical fluids.

Ideally, the pore size is of the order of 10-80 μm diameter. This means that the particle size is generally of the order of 50 μm to 1 mm diameter or preferably of 250-500 μm. As can be seen, the overall particle size will be a function of the pore size. That is, the end application of the matrix will dictate the size of the matrix, of the particles and the pore size. For example, where the matrix is not to be loaded with cells, the pore size becomes less critical, provided that diffusion can still occur through the matrix. Additionally, loose packing increases the pore size such that nutrient or other transfer is better, and vice-versa. However, the pore size is not always a function of the cell size since large pores may be seeded with tiny cells. Use of such particles provides the advantage of ensuring that the overall matrix retains a level of porosity sufficient for cell growth and hence to accommodate the growing tissue. Preferably, the particles are rough at least on their outer surface so that pores may still be formed between close packed particles. Additionally, the provision of a rough surface to the particle improves adhesion of cells to the particle.

The matrix may comprise additional phases using, for example, another polymer phase or an inorganic phase. Examples of inorganic materials comprised in the or each additional phase include bioglasses, ceramics, hydroxyapatites, glasses, glass ceramics and composite materials.

Factors useful for the promotion of tissue growth and development may be added to either or both phases or may be used to coat the particles. Additionally, different factors may be added to each of the phases or to the or each coating. Factors which may usefully be added include, but are not limited to, epidermal growth factor, platelet derived growth factor, basic fibroblast growth factor, vascular endothelial growth factor, insulin-like growth factor, nerve growth factor, hepatocyte growth factor, transforming growth factors and bone morphogenic proteins, cytokines including interferons, interleukins, monocyte chemotactic protein-1 (MCP-1), oestrogen, testosterone, kinases, chemokinases, glucose or other sugars, amino acids, calcification factors, dopamine, amine-rich oligopeptides, such as heparin binding domains found in adhesion proteins such as fibronectin and laminin, other amines tamoxifen, cis-platin, peptides and certain toxoids. Additionally, drugs, hormones, enzymes, nutrients or other therapeutic agents or factors or mixtures thereof may be added to one or both of the phases. Again, different drugs, hormones, enzymes, antibiotics, nutrients or other therapeutic agents or factors or mixtures thereof may be added to each of the phases.

However, as mentioned above, the present inventors have found that the matrix may be used as a tissue scaffold without the need to introduce cells. When the tissue scaffold (without cells) is placed in or at a site where it is needed local, endogenous cells can be recruited to or encouraged to grow on, in or about the scaffold. This effect is enhanced by the presence of one or more of the above described growth factors in the scaffold.

The tissue formed according to the method of the present invention may be used in vivo as implanted tissue or in vitro as tissue cultures. For example, the tissues may be used in vivo to replace removed diseased, damaged or non-functioning tissues or in vitro as a tissue culture. Advantageously, the present invention allows the production or generation of a 3-dimensional culture tissue which is useful as a research tool such as in the study of drug diffusion or uptake or in the use of secretory cells which often require the cells to be in a 3-dimensional arrangement for secretion to occur.

Where the matrix is to be used in a tissue it is preferably introduced to the tissue prior to solidification.

In a preferred embodiment, where the tissue is to be used in vivo, it is preferred that the first phase transforms to a solid or semi-solid state at or close to the body temperature of the animal, or at or close to the pH of the appropriate tissue. Alternatively, setting agents may be used to accelerate solidification. In any event, it is preferred that the conditions needed to cause solidification of the first phase are not detrimental to any cells entrained therein.

The present invention also provides a kit for the formation of a tissue scaffolding matrix as hereindescribed.

In one preferred embodiment of the invention, the first phase comprises a polymer having a low glass transition temperature (Tg) or melting point polymer, for example below 45° C., preferably, below 40° C. and ideally at or below 37° C., and the second phase comprises a polymer having a higher glass transition temperature or melting point, for example >55° C. The first phase is heated above 45° C., preferably above 40° C. and ideally above 37° C. in order to render the polymer tacky or fully liquefied, the second phase is introduced to the first phase and mixed. The mixture is allowed to cool. Where cells are to be present in the matrix they may be added to the second phase prior to its introduction to the first phase or more preferably before solidification of the matrix. Either phase may further comprise growth factors or other pharmacologically active compounds to achieve a controlled release effect in use.

The pore structure is formed by gaps between particles of the or each phase or by the incomplete liquefaction of the first phase in addition to the inherent porosity of the particles themselves.

In a second embodiment, the matrix is preferably formed by gelation. In this embodiment, the first phase comprises a material which gels in relation to temperature, for example agarose, or pH, for example acrylimide, or to the addition of a setting or gelling agent, such as the addition of thrombin to fibrinogen to produce a fibrin gel. The first phase is brought into a fluid or liquid state and is then mixed with a non-gelling, preferably solid, second phase. The mixture is allowed to cool or to gel. Cells may be added to the second phase prior to mixing with the first, or after mixing but before full gelling of the gel has occurred.

Embodiments of the invention will now be described with reference to the following examples and as illustrated by FIGS. 1 to 3 of the attached drawings, in which

DETAILED DESCRIPTION OF THE INVENTION

Example 1

Cross-Linking Via Temperature Triggered Solidification

Figure 1:
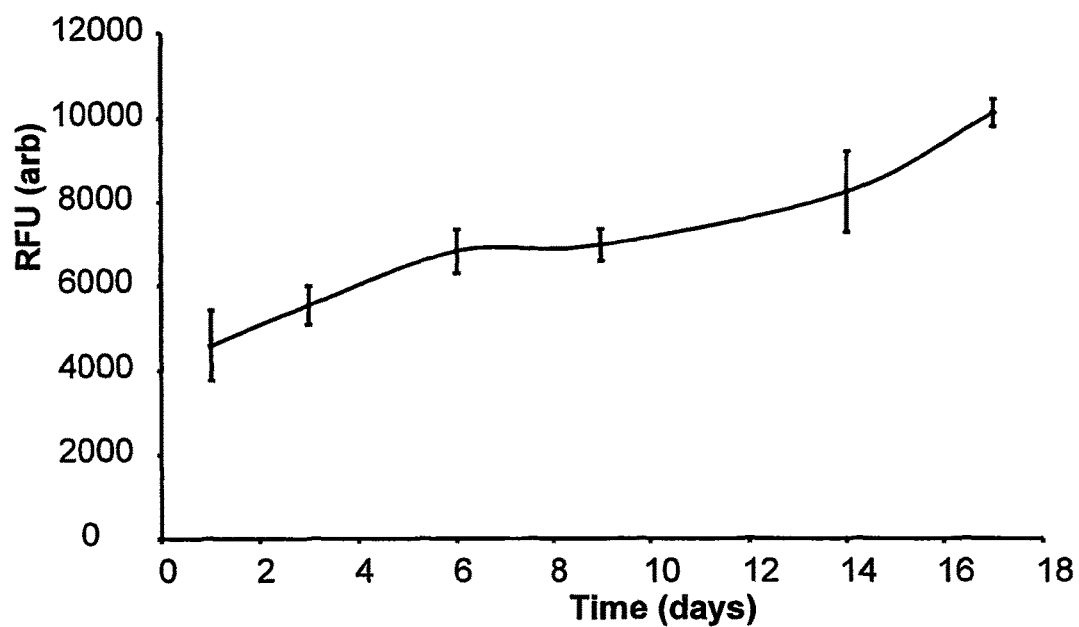
FIG. 1 is a graph showing cell growth on temperature crosslinked 15% $PEG_{1000}$/PLGA measured using Resazurin reduction assay. Values show relative fluorescent units from reduced reaction product after subtraction of cell free controls (n=3,±SD)

In this example, the first phase comprises poly (ethylene glycol)/poly (DL-Lactide) blend particles (10 wt % polyethylene glycol) and the second phase comprises porous poly (DL-Lactide) particles manufactured by conventional particulate leaching methods. The two components are mixed together (at a range of ratios between 20:80 and 80:20) and then heated to 60° C. to produce a malleable material, which is shaped by the surgeon and applied to the defect site. In this example the first phase does not fully liquefy but becomes a 'tacky' semi-solid at the processing temperature (above the polymers glass transition temperature). In another example, the first phase (of a different polymer blend composition) may be fully liquefied (above the polymers melting transition) at 40-60° C., upon which porous particles of the second phase are mixed together with the still liquid first phase. The material is then shaped and applied to the defect site by the surgeon.

Example 1A

Temperature Triggered Solidification

Further examples of polymer blend compositions, their glass transition temperatures (measured using differential scanning calorimetry) and crosslinking temperatures are shown in the table below.

| Material | Glass Transition Temperature (° C.) | Crosslinking Temperature (° C.) |
| --- | --- | --- |
| $P_{DL}LA$ | 48 | 75-80° C. |
| 15% $PEG_{3400}/P_{DL}LA$ | 23 | 55-65° C. |
| 20% Poly (caprolactone diol$_{530}$)/$P_{DL}LA$ | 23 | 50-55° C. |
| 15% $PEG_{400}/P_{DL}LA$ | 15 | 45° C. |
| 20% $PEG_{1000}/P_{DL}LA$ | 8 | 37-40° C. |
| 10% DL-Lactide/$P_{DL}LA$ | 46 | 65-70° C. |
| PLGA | 43 | 70° C. |
| 15% $PEG_{1000}$/PLGA | 16 | 37-40° C. |

Example 1b

Temperature Triggered Crosslinking With Cell Seeding

Melt blends were manufactured by heating components (1.7 g PLGA, 0.3 g $PEG_{1000}$) on a ceramic tile placed on a hotplate and physically mixing components in the melt state. The material was cooled, removed from the tile, and immediately cut and ground after cooling in liquid nitrogen. The ground blends were stored in a vacuum desicator prior to use. Glass transition temperatures were measured using differential scanning calorimetry with the temperature being taken from the midpoint of the transition region. The glass transition temperature of PLGA was measured at 43° C. and that of the blend at 16° C.

Cell growth in static culture was measured upon scaffolds (triplicate repeats) seeded with human dermal fibroblasts (and cell free controls). Ground blend material (80 mgs of 15% $PEG_{1000}$/5050DL ground blend) was pre-sintered in a 6 mm PDMS mould at 37° C. for 15 minutes. A cell suspension was then added to the material ($5\times10^5$ human dermal fibroblasts (@ p8, 50 year old donor/facial biopsy) in 100 µl of complete medium) and the material was compressed with a spatula and sintered for a further 1 hour at 37° C. The scaffolds were then removed from the PDMS moulds and placed in complete culture medium. Cell free controls were prepared by substituting 100 µl of complete medium for the cell suspension. The scaffolds were cultured for 17 days (static culture) in complete media with full media changes every 3-4 days.

Cell growth and proliferation were measured using a resazurin reduction assay (FIG. 1) with readings taken every 3-4 days. The scaffolds were removed from culture, washed in PBS and placed in 1 ml of a 10 µg/ml resazurin solution in serum free media for 1 hour. The solution was then aliquotted (3×150 µl) into a 96 well plate and fluorescence intensity read on a plate reader with an excitation frequency of 530 nm and an emission frequency of 590 nm.

Example 2

Solidification By Gelation

In this example the first phase is composed of a solution of Pluronics F127 (20 wt % in buffer or media), which undergoes a liquid to gel transition above 25° C. The second phase comprises porous particles of poly (DL-Lactide) manufactured by conventional particulate leaching methods. The two components are mixed (over a large range of possible ratios, for example 100 µls of phase 1 with 100 mgs of phase 2) and held as a liquid below room temperature. The components are then delivered via injection to the defect site, where the material gels upon reaching 37° C.

Example 3

Solidification By Gelation

In this example the first phase is comprised of a solution of fibrinogen (for example of between 30 to 200 mg/ml in buffer or media), which is gelled upon addition of thrombin. The second phase comprises porous particles of poly (DL-Lactide) manufactured by conventional particulate leaching methods. The two components are mixed (over a large range of possible ratios, for example 100 µls of phase 1 with 100 mgs of phase 2) and held as a liquid in a syringe ready for injection. Upon injection to the defect site they are mixed (using a dual barrel syringe) with a solution of thrombin (yielding a final thrombin concentration of, for example, between 1-1000 Units/ml), which results in the crosslinking and gelation of the first phase.

Example 3a

Crosslinking of Cell Loaded Porous $P_{DL}LA$ Pieces (Large 1-2 mm Pieces)

Porous $P_{DL}LA$ pieces were produced by solvent casting and particulate leaching, using a salt weight fraction of 80%.

A 45 wt % solution of $P_{DL}LA$ in DCM (900 mgs in 2 ml) was mixed with 3.6 g of salt particles (63-106 μm size fraction after grinding and sieving, average size=88±27 μm). The polymer solution with salt was then poured onto a ceramic tile and left overnight for the solvent to evaporate. The polymer salt composite was removed from the tile and manually cut into 1-2 mm sized pieces. The salt was leached from the pieces by immersion in water and stirring overnight.

Cell growth in static culture was measured upon scaffolds (triplicate repeats) seeded with human dermal fibroblasts (and cell free controls). Porous $P_{DL}LA$ pieces (2×120 mgs) were coated in serum (2 mls) via gentle agitation over 1 hour. Cell seeding was carried out by placing 120 mgs of serum coated $P_{DL}LA$ in 1 ml of a cell suspension and agitating gently for 1 hour ($1.2 \times 10^6$ c/ml in serum free media, human dermal fibroblasts @ p8, 50 year donor/facial biopsy). Cell free controls were placed in serum free media for 1 hour. Following cell attachment, the pieces were washed in $Ca^{2+}$ free HBSS. A solution of fibrinogen+ thrombin (160 μl of 100 mg/ml fibrinogen with 10 U/ml thrombin) was added to and mixed with the pieces, the excess liquid was removed and then the pieces allowed to crosslink over 15 minutes. The scaffolds were cultured for 17 days (static culture) in complete media (DMEM supplemented with foetal calf serum) with full media changes every 3-4 days.

Figure 2:
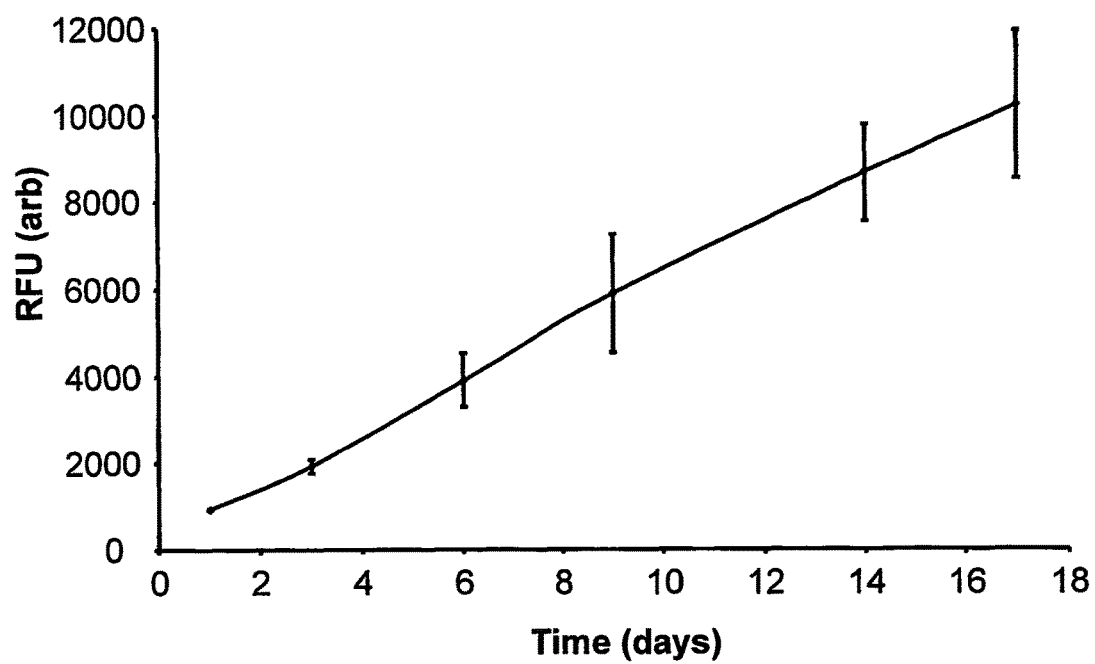
FIG. 2 is a graph showing cell growth on enzymatically crosslinked porous $P_{DL}LA$ pieces measured using Resazurin reduction assay. Values show relative fluorescent units from reduced reaction product after subtraction of cell free controls (n=3,±SD)
Figure 3:
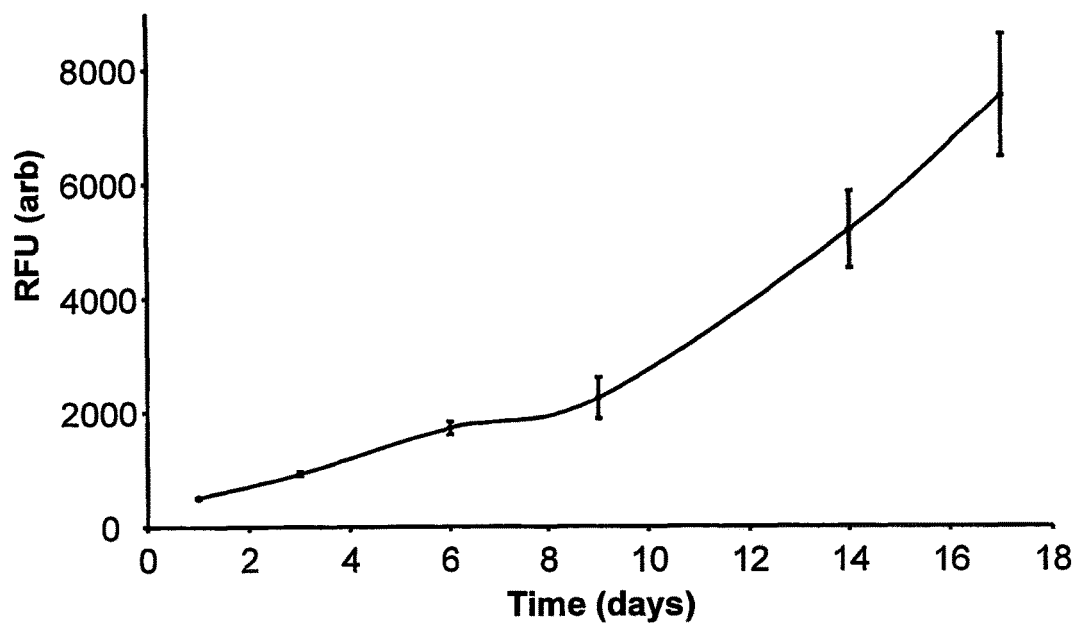
FIG. 3 is a graph showing cell growth on enzymatically crosslinked $P_{DL}LA$ microparticles seeded with human dermal fibroblasts measured using Resazurin reduction assay. Values show relative fluorescent units from reduced reaction product after subtraction of cell free controls (n=3,±SD).

Cell growth and proliferation were measured using a resazurin reduction assay (FIG. 2) with readings taken every 3-4 days. The scaffolds were removed from culture, washed in PBS and placed in 1 ml of a 10 μg/ml resazurin solution in serum free media for 1 hour. The solution was then aliquotted (3×150 μl) into a 96 well plate and fluorescence intensity read on a plate reader with an excitation frequency of 530 nm and an emission frequency of 590 nm.

Example 3b

Crosslinking of Cell Loaded Porous $P_{DL}LA$ Pieces (Small 250-500 μm Pieces)

Porous $P_{DL}LA$ pieces were produced by solvent casting and particulate leaching, using a salt weight fraction of 90%. A 45 wt % solution of $P_{DL}LA$ in DCM (900 mgs in 2 ml) was mixed with 8.1 g of ground salt particles (unsieved after grinding in pestle and mortar). The polymer solution with salt was then placed on a ceramic tile and left overnight for the solvent to evaporate. The polymer salt composite was removed from the tile and ground using a pestle and mortar. The salt was leached from the pieces by immersion in water and stirring overnight. After salt leaching the porous pieces were sieved and the 250-500 μm fraction retained.

Porous $P_{DL}LA$ pieces (40 mgs) were coated with serum via gentle agitation. The pieces were then washed in PBS. Human dermal fibroblasts (from adult donor @ passage 15) were seeded onto porous pieces by placing the porous pieces in 1 ml of a cell suspension ($9 \times 10^5$ cells/ml) in serum free media and gently stirring for 1 hour.

Following cell attachment, a solution of fibrinogen+ thrombin (160 μl of 100 mg/ml fibrinogen with 5 U/ml thrombin) was added to and mixed with the pieces, the excess liquid was removed and then the pieces allowed to crosslink over 30 minutes.

Cell metabolism and growth on the scaffold were measured over 72 hours. The scaffolds were removed from culture, washed in PBS and placed in 1 ml of a 10 μg/ml resazurin solution in serum free media for 1 hour. The solution was then aliquotted (3×150 μl) into a 96 well plate and fluorescence intensity read on a plate reader with an excitation frequency of 530 nm and an emission frequency of 590 nm. The RFU value from the scaffolds increased from 296 RFU to 569 RFU (after background subtraction) between 24 and 72 hours.

Example 3c

Crosslinking of $P_{DL}LA$ Microparticles and Cells 4 g of $P_{DL}LA$ was dissolved in 20 ml of dichloromethane to produce a 20 wt % solution. Poly (vinyl alcohol), (88% hydrolysed) was dissolved in distilled water to give a 0.05 wt % solution which was filtered through a 0.45 μm filter. The PVA solution was dispersed with a homogeniser at 6,000 rpm for 5 minutes after which the $P_{DL}LA$/DCM solution was injected into the dispersed PVA solution. The mixture was homogenised for a further 5 minutes before being allowed to stir overnight while the DCM evaporated. Microparticles were then washed with distilled water 3 times using a centrifuge prior to being lyophilised. Microparticle diameter was measured at 20 μm (±10 μm) using brightfield microscopy and image analysis.

Human dermal fibroblasts (from 50 year old donor/facial biospy, at passage 8) were resuspended in a small amount of full medium ($5 \times 10^5$ cells in 50 μl). This cell suspension was mixed with 100 μl of a fibrinogen/thrombin solution (150 mg/ml fibrinogen in HBSS with 15 U/ml of Thrombin) and this solution then added to 200 mgs of microparticles and mixed. The resulting paste was placed into a 6 mm PDMS cube shaped mould and placed at 37° C. for 40 minutes to allow crosslinking to complete. Cell free controls were prepared by substituting 50 μl of complete medium for the cell suspension. The scaffolds were cultured for 17 days (static culture) in complete media with full media changes every 3-4 days.

Cell growth and proliferation were measured using a resazurin reduction assay (FIG. 2) with readings taken every 3-4 days. The scaffolds were removed from culture, washed in PBS and placed in 1 ml of a 10 μg/ml resazurin solution in serum free media for 1 hour. The solution was then aliquotted (3×150 μl) into a 96 well plate and fluorescence intensity read on a plate reader with an excitation frequency of 530 nm and an emission frequency of 590 nm.

Example 4

Porous Particles

In this example large porous particles (≥500 μm and up to several mms) are produced by conventional salt leaching techniques. Salt is ground using a pestle and mortar, then sieved with the appropriate size fraction being retained. Ideally the size of the salt particles will be 50-100 μm. The salt particles are then mixed with poly (DL-Lactide), in either the melt phase or in an appropriate solvent. The loading of salt will be between 50 and 90 wt %. The solid monolith of salt/polymer composite (after cooling or solvent extraction) is then processed into large particles either by grinding or cutting. The salt is then leached from the composite by agitating in water for at least 24 hours.

In a further example the salt/polymer composite may be processed by conventional gas foaming techniques using for example supercritical $CO_2$. In a further example porous polymer pieces may be fabricated by conventional gas foaming techniques, using for example supercritical $CO_2$.

The invention claimed is:

1. A porous polymeric composition in particulate or powder form, comprising:
    a first phase comprising a first polymer and a plasticizer selected from the group consisting of polyethylene glycol (PEG), polypropylene glycol, polycaprolactone, low molecular weight oligomers of polyethylene glycol (PEG), polypropylene glycol, or polycaprolactone, adipates, phosphates, phthalates, sabacates, azelates, citrates, poly lactides, and poly lactide-co-glycolide;
    a second phase comprising a second polymer,
    wherein either the first or the second phase has a glass transition temperature of <45° C.,
    wherein the composition forms a porous matrix when the phase having a glass transition temperature of <45° C. is heated to a temperature above its glass transition temperature above and mixed with the other phase,
    wherein the first and the second polymers are selected from the group consisting of poly([a]-hydroxyacids), polylactic or polyglycolic acids, poly-lactide poly-glycolide copolymers, poly-lactide polyethylene glycol (PEG) copolymers, polyesters, poly ([epsilon]-caprolactone), poly (3-hydroxy-butyrate), poly (s-caproic acid), poly (p-dioxanone), poly (propylene fumarate), poly (ortho esters), polyol/diketene acetals addition polymers, polyanhydrides, poly (sebacic anhydride) PSA), poly(carboxybiscarboxyphenoxyphenoxy hexane) (PCPP), poly rbis (p-carboxyphenoxy) methanel (PCPM), copolymers of SA, CPP and CPM poly (amino acids), poly (pseudo amino acids), polyphosphazenes, derivatives of poly [(dichloro) phosphazene], poly [(organo) phosphazenes] polymers, polyphosphates, polyethylene glycol polypropylene block copolymers, natural polymers, silk, elastin, chitin, chitosan, fibrin, fibrinogen, polysaccharides (including pectins), alginates, collagen, poly (amino acids), peptides, polypeptides, proteins, co-polymers prepared from the monomers of these polymers, or mixtures thereof.

2. The composition according to claim 1, wherein the mixture of the first and second phase is porous and further incorporates cells from a target tissue site.

3. The composition according to claim 1, wherein the second phase is porous.

4. The composition according to claim 3, wherein the second phase has a porosity of from 10% to 97%.

5. The composition according to claim 1, wherein each polymer is biodegradable.

6. The composition according to claim 1, wherein the second phase is porous and further incorporates cells therein from a target tissue site.

7. The composition according to claim 1, further comprising cells.

8. The composition according to claim 1, further comprising one or more factors useful for promotion of tissue growth and development.

9. The composition according to claim 1, wherein the first and the second phase each further comprises drugs, hormones, enzymes, antibiotics, or nutrients, or mixtures thereof.

10. The composition according to claim 9,
    wherein drugs, hormones, enzymes, antibiotics, or nutrients, or mixtures thereof that are comprised within the first phase are different than those comprised within the second phase.

11. The composition of claim 1, wherein the first polymer is the same as the second polymer.

* * * * *